United States Patent

[19]

Gutterer

[11] Patent Number: 6,121,279

[45] Date of Patent: Sep. 19, 2000

[54] SUBSTITUTED 6-PHENYLPHENANTHRIDINES

[75] Inventor: Beate Gutterer, Allensbach, Germany

[73] Assignee: Byk Gulden Lomberg Chemische Fabrik GmbH, Konstanz, Germany

[21] Appl. No.: 09/462,508

[22] PCT Filed: Jul. 18, 1998

[86] PCT No.: PCT/EP98/04478

§ 371 Date: Jan. 24, 2000

§ 102(e) Date: Jan. 24, 2000

[87] PCT Pub. No.: WO99/05113

PCT Pub. Date: Feb. 4, 1999

[30] Foreign Application Priority Data

Jul. 25, 1997 [AT] Austria ................................. 97112793

[51] Int. Cl.$^7$ .......................... A61K 31/44; C07D 221/12
[52] U.S. Cl. ............................................. 514/298; 546/109
[58] Field of Search .............................. 546/109; 514/298

[56] References Cited

PUBLICATIONS

Kametani et al., "Cyclised Products in the Synthesis of 6–Substituted Phenanthridines by Phenolic Cyclisation." J. Chem. Soc., Section C: Organic Chemistry, pp. 1805–1808, 1971.

*Primary Examiner*—Barbara Badio
*Attorney, Agent, or Firm*—Jacobson, Price, Holman & Stern, PLLC

[57] ABSTRACT

The invention relates to compounds of formula (I):

wherein R1, R2, R3, R31, R4, R5, R51 and R6 are as defined in the specification. The compounds are phosphodiesterase inhibitors. Also disclosed are pharmaceutical compositions and methods of use of the compounds.

11 Claims, No Drawings

SUBSTITUTED 6-PHENYLPHENANTHRIDINES

This application is a 371 of PCT/EP98/04478 filed Jul. 18, 1998.

FIELD OF APPLICATION OF THE INVENTION

The invention relates to novel 6-phenylphenanthridines which are used in the pharmaceutical industry for the production of medicaments.

KNOWN TECHNICAL BACKGROUND

Chem. Ber. 1939, 72, 675–677, J. Chem. Soc., 1956, 4280–4283 and J. Chem. Soc. (C), 1971, 1805 describes the synthesis of 6-phenylphenanthridines.

DESCRIPTION OF THE INVENTION

It has now been found that the novel 6-phenylphenanthridines which are described below in greater detail have surprising and particularly advantageous properties.

The invention thus relates to compounds of the formula I

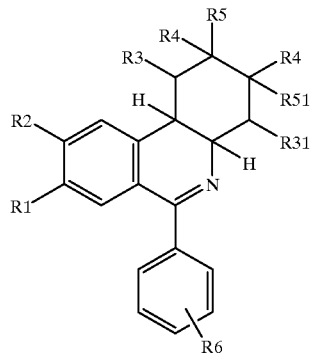

(I)

in which
R1 is hydroxyl, 1–4C-alkoxy, 3–7C-cycloalkoxy, 3–7C-cycloalkylmethoxy or completely or predominantly fluorine-substituted 1–4C-alkoxy,
R2 is hydroxyl, 1–4C-alkoxy, 3–7C-cycloalkoxy, 3–7C-cycloalkylmethoxy or completely or predominantly fluorine-substituted 1–4C-alkoxy,
or in which
R1 and R2 together are a 1–2C-alkylenedioxy group,
R3 is hydrogen or 1–4C-alkyl,
R31 is hydrogen or 1–4C-alkyl,
or in which
R3 and R31 together are a 1–4C-alkylene group,
R4 is hydrogen or 1–4C-alkyl,
R5 is hydrogen,
R51 is hydrogen,
or in which
R5 and R51 together are an additional bond,
R6 is $SO_2$—N(R7)R8 or CO—N(R9)R10, where
R7 and R8 independently of one another are hydrogen, 1–7C-alkyl, 3–7C-cycloalkyl, 3–7C-cycloalkylmethyl or an unsubstituted or R12- and/or R13-substituted phenyl radical, or where R7 and R8, together and including the nitrogen atom to which both are bonded, are a 1-pyrrolidinyl, 1-piperidyl, 1-hexahydroazepinyl or 4-morpholinyl radical,
R9 is hydrogen or 1–4C-alkyl,
R10 is an unsubstituted or R11-substituted pyridyl radical or an unsubstituted or R12- and/or R13-substituted phenyl radical, where
R11 is halogen, nitro, carboxyl, 1–4C-alkoxy, 1–4C-alkoxycarbonyl, 1–4C-alkyl, trifluoromethyl or completely or predominantly fluorine-substituted 1–4C-alkoxy,
R12 is hydroxyl, halogen, 1–4C-alkyl or 1–4C-alkoxy,
R13 is hydroxyl, halogen, nitro, cyano, carboxyl, 1–4C-alkyl, trifluoromethyl, 1–4C-alkoxy, 1–4C-alkoxycarbonyl, 1–4C-alkylcarbonyloxy, amino, mono- or di-1–4C-alkylamino, aminocarbonyl, mono- or di-1–4C-alkylaminocarbonyl or completely or predominantly fluorine-substituted 1–4C-alkoxy,
and the salts of these compounds.

1–4C-Alkyl represents a straight-chain or branched alkyl radical having 1 to 4 carbon atoms. Examples which may be mentioned are the butyl, isobutyl, sec-butyl, tert-butyl, propyl, isopropyl and, preferably, the ethyl and methyl radicals.

1–4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and, preferably, the ethoxy and methoxy radicals.

3–7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

Completely or predominantly fluorine-substituted 1–4C-alkoxy which may be mentioned are, for example, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and, preferably, the difluoromethoxy radicals. "Predominantly" in this connection means that more than half of the hydrogen atoms are substituted by fluorine atoms.

1–2C-Alkylenedioxy represents, for example, the methylenedioxy (—O—$CH_2$—O—) and the ethylenedioxy radicals (—O—$CH_2$—$CH_2$—O—).

If R3 and R31 together have the meaning 1–4C-alkylene, the positions 1 and 4 in compounds of the formula I are linked to one another by a 1–4C-alkylene bridge, 1–4C-alkylene representing straight-chain or branched alkylene radicals having 1 to 4 carbon atoms. Examples which may be mentioned are the radicals methylene (—$CH_2$—), ethylene (—$CH_2CH_2$—), trimethylene (—$CH_2$—$CH_2$—$CH_2$—), 1,2-dimethylethylene [—CH($CH_3$)—CH($CH_3$)—] and isopropylidene [—C($CH_3$)$_2$—].

If R5 and R51 together are an additional bond, then the carbon atoms in the positions 2 and 3 in compounds of the formula I are linked to one another via a double bond.

1–7C-Alkyl represents straight-chain or branched alkyl radicals having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

3–7C-Cycloalkyl represents cyclopropyl, cyclobutyl, cyclopentyl, cyclohexyl and cycloheptyl, of which cyclopropyl, cyclobutyl and cyclopentyl are preferred.

3–7C-Cycloalkylmethyl represents a methyl radical which is substituted by one of the abovementioned 3–7C-cycloalkyl radicals. The 3–5C-cycloalkylmethyl radicals cyclopropylmethyl, cyclobutylmethyl and cyclopentylmethyl may be mentioned preferably.

Halogen within the meaning of the invention is bromine, chlorine or fluorine.

1–4C-Alkoxycarbonyl represents a carbonyl group to which one of the abovementioned 1–4C-alkoxy radicals is bonded. Examples which may be mentioned are the methoxycarbonyl ($CH_3O—C(O)—$) and the ethoxycarbonyl ($CH_3CH_2O—C(O)—$) radicals.

1–4C-Alkylcarbonyloxy represents a carbonyloxy group to which one of the abovementioned 1–4C-alkyl radicals is bonded. An example which may be mentioned is the acetoxy radical ($CH_3C(O)—O—$).

In addition to the nitrogen atom, mono- or di-1–4C-alkylamino radicals contain one or two of the abovementioned 1–4C-alkyl radicals. Di-1–4C-alkylamino is preferred and here, in particular, dimethyl-, diethyl- or diisopropylamino.

In addition to the carbonyl group, mono- or di-1–4C-alkylaminocarbonyl radicals contain one of the abovementioned mono- or di-1–4C-alkylamino radicals. Examples which may be mentioned are the N-methyl, the N,N-dimethyl, the N-ethyl, the N-propyl, the N,N-diethyl and the N-isopropylamino-carbonyl radicals.

Exemplary R11-substituted pyridyl radicals which may be mentioned are the radicals 2-chloropyrid-4-yl, 3-nitropyrid-4-yl, 2-methylpyrid-4-yl, 3-fluoropyrid-4-yl, 3-carboxypyrid-4-yl, 2-ethoxypyrid-4yl 3-fluoropyrid-5-yl, 2-dimethylaminopyrid-5-yl, 2-chloropyrid-3-yl, 4-trifluoromethylpyrid-3-yl, 2-methoxypyrid-5-yl, 2-nitropyrid-3-yl, 3-methylpyrid-5-yl, 3-carboxypyrid-2-yl, 3-ethoxypyrid-2-yl, 5-nitropyrid-2-yl and 4-methoxycarbonylpyrid-3-yl.

Exemplary R12- and/or R13-substituted phenyl radicals which may be mentioned are the radicals 4-acetoxyphenyl, 3-aminophenyl, 4-aminophenyl, 2-bromophenyl, 4-bromophenyl, 2-chlorophenyl, 3-chlorophenyl, 4-chlorophenyl, 3-bromophenyl, 2,3-dichlorophenyl, 2,4-dichlorophenyl, 2-chloro-4-nitrophenyl, 4-diethylamino-2-methylphenyl, 4-methoxyphenyl, 3-methoxyphenyl, 2-chloro-5-nitrophenyl, 4-chloro-3-nitrophenyl, 2,6-dichlorophenyl, 3,5-dichlorophenyl, 2,5-dichlorophenyl, 2,6-dibromophenyl, 2-cyanophenyl, 3-cyanophenyl, 4-cyanophenyl, 4-diethylaminophenyl, 4-dimethylaminophenyl, 2-fluorophenyl, 4-fluorophenyl, 3-fluorophenyl, 2,4-difluorophenyl, 2,6-difluorophenyl, 2-chloro-6-fluorophenyl, 2-fluoro-5-nitrophenyl, 2-hydroxyphenyl, 3-hydroxyphenyl, 3,4-dichlorophenyl, 4-hydroxyphenyl, 4-hydroxy-3-methoxyphenyl, 2-hydroxy-4-methoxyphenyl, 2,4-dihydroxyphenyl, 2-methoxphenyl, 2,3-dimethoxyphenyl, 3,4-dimethoxyphenyl, 2,4-dimethoxyphenyl, 2-dimethylaminophenyl, 2-methylphenyl, 3-methylphenyl, 4-methylphenyl, 2-chloro-6-methylphenyl, 4-methyl-3-nitrophenyl, 2,4-dimethylphenyl, 2,6-dimethylphenyl, 2,3-dimethylphenyl, 2-nitrophenyl, 3-nitrophenyl, 4-nitrophenyl, 4-ethoxyphenyl, 2-trifluoromethylphenyl, 4-trifluoromethylphenyl, 3-trifluoromethylphenyl, 4-trifluoromethoxyphenyl, 3-trifluoromethoxyphenyl and 2-trifluoromethoxyphenyl.

Suitable salts for compounds of the formula I—depending on substitution—are all acid addition salts or all salts with bases. Particular mention may be made of the pharmacologically tolerable salts of the inorganic and organic acids and bases customarily used in pharmacy. Those which are suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether it is a mono- or polybasic acid and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts which may be obtained initially as process products, for example in the preparation of the compounds according to the invention on an industrial scale, are converted into pharmacologically tolerable salts by processes known to the person skilled in the art.

It is known to the person skilled in the art that the compounds according to the invention and their salts, when, for example, they are isolated in crystalline form, can contain various amounts of solvents. The invention therefore also includes all solvates and in particular all hydrates of the compounds of the formula I, and all solvates and in particular all hydrates of the salts of the compounds of the formula I.

Compounds of the formula I to be emphasized are those in which

R1 is 1–4C-alkoxy, 3–7C-cycloalkoxy, 3–7C-cycloalkylmethoxy or completely or predominantly fluorine-substituted 1–2C-alkoxy, R2 is 1–4C-alkoxy, 3–7C-cycloalkoxy, 3–7C-cycloalkylmethoxy or completely or predominantly fluorine-substituted 1–2C-alkoxy, R3 is hydrogen, R31 is hydrogen, or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is SO$_2$—N(R7)R8 or CO—N(R9)R10, where
R7 and R8 independently of one another are hydrogen, 1–4C-alkyl, 3–7C-cycloalkyl, 3–7C-cycloalkylmethyl or an unsubstituted or R12- and/or R13-substituted phenyl radical, or where R7 and R8, together and including the nitrogen atom to which both are bonded, are a 1-piperidyl or 4-morpholinyl radical,
R9 is hydrogen,
R10 is an unsubstituted or R11-substituted pyridyl radical or an unsubstituted or R12- and/or R13-substituted phenyl radical, where
R11 is halogen, 1–4C-alkoxy, 1–4C-alkyl, trifluoromethyl or completely or predominantly fluorine-substituted 1–4C-alkoxy,
R12 is hydroxyl, halogen, 1–4C-alkyl or 1–4C-alkoxy,
R13 is hydroxyl, halogen, nitro, cyano, carboxyl, 1–4C-alkyl, trifluoromethyl, 1–4C-alkoxy, 1–4C-alkoxycarbonyl, 1–4C-alkylcarbonyloxy or completely or predominantly fluorine-substituted 1–4C-alkoxy,
and the salts of these compounds.

An embodiment [embodiment a)] of the compounds according to the invention are compounds of the formula I in which
R1 is 1–4C-alkoxy, 3–7C-cycloalkoxy, 3–7C-cycloalkylmethoxy or completely or predominantly fluorine-substituted 1–2C-alkoxy,
R2 is 1–4C-alkoxy, 3–7C-cycloalkoxy, 3–7C-cycloalkylmethoxy or completely or predominantly fluorine-substituted 1–2C-alkoxy,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is SO$_2$—N(R7)R8, where
R7 and R8 independently of one another are hydrogen, 1–4C-alkyl, 3–7C-cycloalkyl, 3–7C-cycloalkylmethyl or an unsubstituted or R12- and/or R13-substituted phenyl radical, or where R7 and R8, together and including the nitrogen atom to which both are bonded, are a 1-piperidyl or 4-morpholinyl radical,
R12 is hydroxyl, halogen, 1–4C-alkyl or 1–4C-alkoxy,
R13 is hydroxyl, halogen, nitro, cyano, carboxyl, 1–4C-alkyl, trifluoromethyl, 1–4C-alkoxy, 1–4C-alkoxycarbonyl, 1–4C-alkylcarbonyloxy or completely or predominantly fluorine-substituted 1–4C-alkoxy,
and the salts of these compounds.

Compounds of embodiment a) to be emphasized are compounds of formula I in which
R1 is 1–4C-alkoxy, 3–7C-cycloalkoxy or completely or predominantly fluorine-substituted 1–2C-alkoxy,
R2 is 1–4C-alkoxy, 3–7C-cycloalkoxy or completely or predominantly fluorine-substituted 1–2C-alkoxy,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is SO$_2$—N(R7)R8, where
R7 and R8 independently of one another are hydrogen, 1–4C-alkyl, 3–7C-cycloalkyl or an unsubstituted or R13-substituted phenyl radical, where
R13 is halogen, nitro, cyano, 1–4C-alkyl, trifluoromethyl, 1–4C-alkoxy, 1–4C-alkoxycarbonyl, 1–4C-alkylcarbonyloxy or completely or predominantly fluorine-substituted 1–4C-alkoxy,
and the salts of these compounds.

Compounds of embodiment a) particularly to be emphasized are compounds of the formula I in which
R1 is 1–4C-alkoxy,
R2 is 1–4C-alkoxy,
R3, R31 and R4 are hydrogen,
R5 is hydrogen,
R51 is hydrogen,
or in which
R5 and R51 together are an additional bond,
R6 is SO$_2$—N(R7)R8, where
R7 and R8 independently of one another are hydrogen, 1–4C-alkyl or an unsubstituted or R13-substituted phenyl radical, where
R13 is halogen, cyano, 1–4C-alkyl or 1–4C-alkoxy,
and the salts of these compounds.

Another embodiment [embodiment b)] of the compounds according to the invention are those compounds of the formula I in which
R1 is 1–4C-alkoxy, 3–7C-cycloalkoxy, 3–7C-cycloalkylmethoxy or completely or predominantly fluorine-substituted 1–2C-alkoxy,
R2 is 1–4C-alkoxy, 3–7C-cycloalkoxy, 3–7C-cycloalkylmethoxy or completely or predominantly fluorine-substituted 1–2C-alkoxy,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is CO—N(R9)R10, where
R9 is hydrogen,
R10 is an unsubstituted or R11-substituted pyridyl radical or an unsubstituted or R12- and/or R13-substituted phenyl radical, where R11 is halogen, 1–4C-alkoxy, 1–4C-alkyl, trifluoromethyl or completely or predominantly fluorine-substituted 1–4C-alkoxy, R12 is hydroxyl, halogen, 1–4C-alkyl or 1–4C-alkoxy, R13 is hydroxyl, halogen, nitro, cyano, carboxyl, 1–4C-alkyl, trifluoromethyl, 1–4C-alkoxy, 1–4C-alkoxycarbonyl, 1–4C-alkylcarbonyloxy or completely or predominantly fluorine-substituted 1–4C-alkoxy, and the salts of these compounds.

Compounds of embodiment b) to be emphasized are compounds of the formula I in which R1 is 1–4C-alkoxy, 3–7C-cycloalkoxy or completely or predominantly fluorine-substituted 1–2C-alkoxy, R2 is 1–4C-alkoxy, 3–7C-cycloalkoxy or completely or predominantly fluorine-substituted 1–2C-alkoxy, R3 is hydrogen, R31 is hydrogen, or in which R3 and R31 together are a 1–2C-alkylene group, R4 is hydrogen or 1–4C-alkyl, R5 is hydrogen, R51 is hydrogen, or in which R5 and R51 together are an additional bond, R6 is CO—N(R9)R10, where R9 is hydrogen, R10 is an unsubstituted or R11-substituted pyridyl radical or an unsubstituted or R13-substituted phenyl radical, where R11 is halogen, 1–4C-alkoxy, 1–4C-alkyl or trifluoromethyl, R13 is halogen, nitro, cyano, 1–4C-alkyl, trifluoromethyl, 1–4C-alkoxy, 1–4C-alkoxycarbonyl, 1–4C-alkylcarbonyloxy or completely or predominantly fluorine-substituted 1–4C-alkoxy, and the salts of these compounds.

Compounds of embodiment b) particularly to be emphasized are compounds of the formula I in which R1 is 1–4C-alkoxy, R2 is 1–4C-alkoxy, R3, R31 and R4 are hydrogen, R5 is hydrogen, R51 is hydrogen, or in which R5 and R51 together are an additional bond, R6 is CO—N(R9)R10, where R9 is hydrogen, R10 is an unsubstituted pyridyl radical or an unsubstituted or R13-substituted phenyl radical, where R13 is halogen, cyano, 1–4C-alkyl or 1–4C-alkoxy, and the salts of these compounds.

Preferred compounds of the formula I are those in which

R1 is 1–2C-alkoxy,

R2 is 1–2C-alkoxy,

R3, R31, R4, R5 and R51 are hydrogen,

R6 is SO₂—N(R7)R8 or CO—N(R9)R10, where

R7 is hydrogen or n-propyl,

R8 is hydrogen, n-propyl or p-toluyl,

R9 is hydrogen,

R10 is pyrid-3-yl or 4-cyanophenyl, and the salts of these compounds.

The compounds of the formula I are chiral compounds having chiral centers in the positions 4a and 10b and, depending on the meaning of the substituents R3, R31, R4, R5 and R51, further chiral centers in the positions 1, 2, 3 and 4.

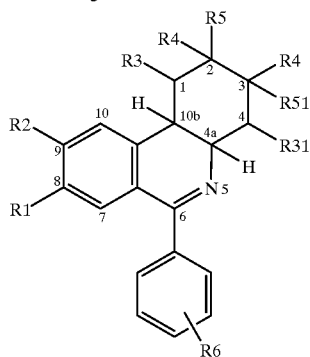

(I)

Numbering:

The invention therefore includes all conceivable pure diastereomers and pure enantiomers and their mixtures in any mixing ratio, including the racemates. The compounds of the formula I are preferred in which the hydrogen atoms in the positions 4a and 10b are cis to one another. Particularly preferred here are the pure cis diastereomers and the pure cis enantiomers and their mixtures in any mixing ratio and including the racemates.

The enantiomers can be separated in a manner known per se (for example by preparation and separation of appropriate diastereoisomeric compounds). Preferably, a separation of enantiomers takes place at the stage of the starting compounds of the formula IV

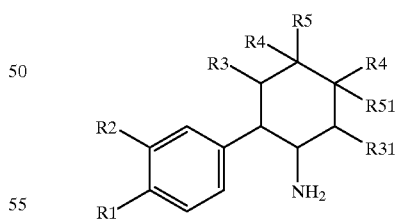

(IV)

for example via salt formation of the racemic compounds of the formula IV with optically active carboxylic acids. Alternatively, enantiomerically pure starting compounds of the formula IV can also be prepared via asymmetric syntheses.

The invention further relates to a process for the preparation of the compounds of the formula I, in which R1, R2, R3, R31, R4, R5, R51 and R6 have the meanings indicated above, and their salts.

The process comprises cyclocondensing compounds of the formula II

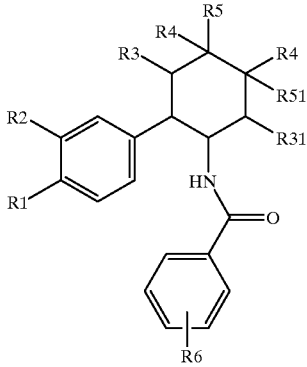

(II)

in which R1, R2, R3, R31, R4, R5, R51 and R6 have the meanings indicated above, and, if desired, then converting the compounds of the formula I obtained into their salts, or, if desired, then converting salts of the compounds of the formula I obtained into the free compounds.

If desired, compounds of the formula I obtained can be converted into further compounds of the formula I by derivatization. For example, it is possible from compounds of the formula I in which R6 is $SO_2$—N(R7)R8 or CO—N(R9)R10 and R7, R8 or R10 is an R12- and/or R13-substituted phenyl radical and a) R13 is an ester group, to obtain the corresponding acids by acidic and alkaline hydrolysis, or to prepare the corresponding amides by reaction with suitably substituted amines;

b) R13 is a 1–4C-alkylcarbonyloxy group, to obtain the corresponding hydroxyl compounds by acidic or alkaline hydrolysis;

c) R13 is a nitro group, to obtain the corresponding amino compounds by selective catalytic hydrogenation, which for their part can in turn be further derivatized.

The methods cited under a), b) and c) are expediently carried out analogously to the methods known to the person skilled in the art.

Cyclocondensation is carried out in a manner known per se to the person skilled in the art according to Bischler-Napieralski (e.g. as described in J. Chem. Soc., 1956, 4280–4282) in the presence of a suitable condensing agent, such as, for example, polyphosphoric acid, phosphorus pentachloride, phosphorus pentoxide, or preferably phosphorus oxychloride, in a suitable inert solvent, e.g. in a chlorinated hydrocarbon such as chloroform, or in a cyclic hydrocarbon such as toluene or xylene, or another inert solvent such as acetonitrile, or without further solvent using an excess of condensing agent, preferably at elevated temperature, in particular at the boiling temperature of the solvent or condensing agent used.

Compounds of the formula II, in which R1, R2, R3, R31, R4, R5, R51 and R6 have the meanings indicated above, are accessible from the corresponding compounds of the formula IV, in which R1, R2, R3, R31, R4, R5 and R51 have the meanings indicated above, by reaction with compounds of the formula III

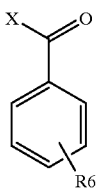

(III)

in which R6 has the meaning indicated above and X is a suitable leaving group, preferably a chlorine atom. For example, the acylation or benzoylation is carried out as in the following examples or as described in J. Chem. Soc. (C), 1971, 1805–1808.

Compounds of the formula III and compounds of the formula IV are either known or can be prepared in a known manner.

Compounds of the formula III in which R6 has the meanings indicated above are obtainable, for example, starting from the phenyl dicarboxylic acids (phthalic acid, isophthalic acid and terephthalic acid) by monoester/monoacid halide formation, reaction with a suitably substituted aniline or aminopyridine and subsequent acid halide formation from the monoester group.

The compounds of the formula IV can be prepared, for example, from compounds of the formula V

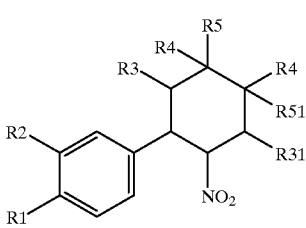

(V)

in which R1, R2, R3, R31, R4, R5 and R51 have the meanings mentioned above, by reduction of the nitro group.

Reduction is carried out in a manner known to the person skilled in the art, for example as described in J. Org. Chem. 1962, 27, 4426 or as described in the following examples. Preferably, reduction is carried out by catalytic hydrogenation, e.g. in the presence of Raney nickel, in a lower alcohol such as methanol or ethanol at room temperature and under normal or elevated pressure. If desired, a catalytic amount of an acid, such as, for example, hydrochloric acid, can be added to the solvent.

The compounds of the formula IV, in which R1, R2, R3, R31 and R4 have the meanings indicated above and R5 and R51 together are an additional bond, can be prepared from the corresponding compounds of the formula V by selective reduction of the nitro group in a manner known to the person skilled in the art, for example in the presence of Raney nickel in a lower alcohol as a solvent using hydrazine hydrate as a hydrogen donor.

The compounds of the formula V, in which R1, R2, R3, R31 and R4 have the meanings indicated above and R5 and R51 are hydrogen, are either known or can be prepared from corresponding compounds of the formula V, in which R5 and R51 together are an additional bond. The reaction can be carried out in a manner known to the person skilled in the art, preferably by hydrogenation in the presence of a catalyst, such as, for example, palladium on activated carbon, e.g. as described in J. Chem. Soc. (C), 1971, 1805–1808.

The compounds of the formula V, in which R5 and R51 together are an additional bond, are either known or can be obtained by reaction of compounds of the formula VI

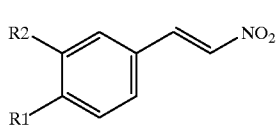

(VI)

in which R1 and R2 have the abovementioned meanings, with compounds of the formula VII,

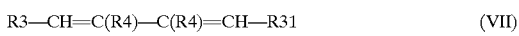 (VII)

in which R3, R31 and R4 have the abovementioned meanings.

Cycloaddition is carried out here in a manner known to the person skilled in the art according to Diels-Alder, e.g. as described in J. Amer. Chem. Soc. 1957, 79, 6559 or in J. Org. Chem. 1952, 17, 581 or as described in the following examples.

Compounds of the formula V obtained in the cycloaddition, in which the phenyl ring and the nitro group are trans to one another, can be converted into the corresponding cis compounds in a manner known to the person skilled in the art, e.g. as described in J. Amer. Chem. Soc. 1957, 79, 6559 or as described in the following examples.

The compounds of the formulae VI and VII are either known or can be prepared in a known manner. The compounds of the formula VI can be prepared, for example, from corresponding compounds of the formula VIII in a manner known to the person skilled in the art, as described, for example, in J. Chem. Soc. 1951, 2524 or in J. Org. Chem. 1944, 9, 170 or as described in the following examples.

The compounds of the formula VIII

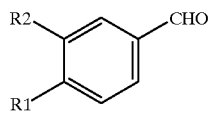

(VIII)

in which R1 and R2 have the meanings indicated above, are either known or can be prepared in a manner known to the person skilled in the art, as described, for example, in Ber. Dtsch. Chem. Ges. 1925, 58, 203.

It is additionally known to the person skilled in the art that in the case of a plurality of reactive centers on a starting or intermediate compound it may be necessary to block one or more reactive centers temporarily by protective groups in order to allow a reaction to proceed specifically at the desired reaction center. A detailed description for the use of a multiplicity of proven protective groups is found, for example, in T. W. Greene, Protective Groups in Organic Synthesis, John Wiley & Sons, 1991.

The isolation and purification of the substances according to the invention are carried out in a manner known per se, for example by distilling off the solvent in vacuo and recrystallizing the resulting residue from a suitable solvent or subjecting it to one of the customary purification methods, such as, for example column chromatography on suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol), which contains the desired acid or base, or to which the desired acid or base is then added. The salts are obtained by filtering, reprecipitation, precipitation with a nonsolvent for the addition salt or by evaporation of the solvent. Salts obtained can be converted by alkalization or by acidification into the free compounds, which in turn can be converted into salts. In this manner, pharmacologically intolerable salts can be converted into pharmacologically tolerable salts.

The following examples serve to explain the invention in greater detail without restricting it. Likewise, further compounds of the formula I whose preparation is not described explicitly can be prepared in an analogous manner or in a manner familiar to the person skilled in the art using customary process techniques.

In the examples, m.p. stands for melting point, h for hour(s), RT for room temperature, EF for empirical formula, MW for molecular weight, calc. for calculated, fnd. for found. The compounds and their salts mentioned in the examples are a preferred subject of the invention.

EXAMPLES

Final Products 1. (+–)-cis-9-Ethoxy-8-methoxy-6-(4-sulfamoylphenyl)-1,2,3,4,4a,10b-hexahydrophenanthridine 700 mg of (+/–)-cis-N-[2-(3-ethoxy-4-methoxyphenyl)cyclohexyl]-4-sulfamoylbenzamide (compound A1) are dissolved in 100 ml of acetonitrile and 2.0 ml of phosphorus oxychloride and the solution is stirred at 80° C. overnight. The reaction mixture is treated with 60 ml of ethyl acetate and extracted with sodium hydrogencarbonate solution. The organic phase is dried using sodium sulfate and concentrated. The residue is recrystallized from ethanol. 420 mg of the title compound are obtained.

EF: $C_{22}H_{26}N_2O_4S$; MW 414.53

Elemental analysis×0.5 $H_2O$:

calc.: C 62.39 H 6.43 N 6.61 S 7.54 fnd.: C 62.50 H 6.52 N 6.34 S 7.36

Starting from the starting compounds described below, the following are obtained according to the procedure as in Example 1:

2. (+/–)-cis-9-Ethoxy-8-methoxy-6-(4-dipropylsulfamoylphenyl)-1,2,3,4,4a,10b-hexahydrophenanthridine EF: $C_{28}H_{38}N_2O_4S$; MW 498.68; m.p.: 107–115° C.

Elemental analysis×HCl:

calc.: C 62.84 H 7.35 N 5.23 S 5.99 Cl 6.62 fnd.: C 62.38 H 7.36 N 5.15 S 5.73 Cl 6.46

3. (+/–)-cis-9-Ethoxy-8-methoxy-6-(4-p-tolylsulfamoylphenyl)-1,2,3,4,4a,10b-hexahydrophenanthridine EF: $C_{29}H_{32}N_2O_4S$; MW 504.65; solidifying oil Elemental analysis:

calc.: C 69.02 H 6.39 N 5.55 S 6.35 fnd.: C 68.59 H 6.74 N 5.68 S 6.15

4. (−)-cis-8,9-Dimethoxy-6-(4-sulfamoylphenyl)-1,2,3,4,4a,10b-hexahydrophenanthridine EF: $C_{21}H_{24}N_2O_4S$; MW 400.50; m.p.: 210–212° C.

Elemental analysis:

calc.: C 62.98 H 6.04 N 6.99 S 8.01 fnd.: C 62.81 H 6.18 N 6.71 S 7.71

Specific rotation $[\alpha]_D^{20} = -83°$ (c=0.2; ethanol)

5. (−)-cis-8,9-Dimethoxy-6-(4-p-tolylsulfamoylphenyl)-1,2,3,4,4a,10b-hexahydrophenanthridine EF: $C_{28}H_{30}N_2O_4S$; MW 490.63; solidifying oil Elemental analysis×0.6 $H_2O$:

calc.: C 67.07 H 6.27 N 5.59 S 6.39 fnd.: C 67.36 H 6.27 N 5.30 S 6.26

Specific rotation $[\alpha]_D^{20} = -54.4°$ (c=0.2; ethanol)

6. (+/−)-cis-9-Ethoxy-8-methoxy-6-(4-pyrid-3-ylamidophenyl)-1,2,3,4,4a,10b-hexahydrophenanthridine 1.49 of (+/−)-cis-N-[2-(3-ethoxy-4-methoxyphenyl)cyclohexyl]-4-pyrid-3-ylamidobenzamide (compound A6) are dissolved in 25 ml of acetonitrile and 0.5 ml of phosphorus oxychloride and the solution is stirred at 80° C. overnight. After cooling, the reaction mixture is treated with methylene chloride and extracted with saturated sodium hydrogencarbonate solution. The organic phase is dried using sodium sulfate and concentrated. The residue is crystallized from ethanol/diethyl ether. 0.92 g of the title compound of m.p. 125–143° C. are obtained.

EF: $C_{28}H_{29}N_3O_3$; MW 455.56

Elemental analysis×$H_2O$:

calc.: C 71.01 H 6.60 N 8.87 fnd.: C 71.12 H 6.74 N 8.62

Starting from the starting compounds described below, the following is obtained according to the procedure as in Example 6:

7. (+/−)-cis-9-Ethoxy-8-methoxy-6-[4-(4-cyanophenylamido)phenyl]-1,2,3,4,4a,10b-hexahydrophenanthridine

EF: $C_{30}H_{29}N_3O_3$; MW 479.3 m.p.: 227–231° C.

Elemental analysis×0.3 $H_2O$:

calc.: C 74.30 H 6.15 N 8.66 fnd.: C 74.36 H 6.18 N 8.53

Startinq Compounds

A1. (+/−)-cis-N-[2-(3-Ethoxy-4-methoxyphenyl)cyclohexyl]-4-sulfamoylbenzamide 3.0 g of (+/−)-cis-2-ethoxy-1-methoxy-4-(2-aminocyclohexyl)benzene (compound B1) are dissolved in 40 ml of methylene chloride and 10 ml of triethylamine. A solution of 3.3 g of p-sulfamoylbenzoyl chloride in 60 ml of methylene chloride is added dropwise at RT, the mixture is extracted after stirring overnight with 100 ml each of water, 2N hydrochloric acid, saturated sodium hydrogencarbonate solution and water again. The organic phase is dried using sodium sulfate and concentrated. The residue is chromatographed on silica gel using a mixture of ethyl acetate/petroleum ether/methanol in the ratio 6/3/1. After concentration of the product fractions, 1.2 g of the title compound of m.p. 129–133° C. are obtained.

Starting from the starting compounds described below, the following are obtained according to the procedure as in Example A1:

A2. (+/−)-cis-4-Dipropylsulfamoyl-N-[2-(3-ethoxy-4-methoxyphenyl)cyclohexyl]benzamide m.p.: 125–137° C.

A3. (+/−)-cis-N-[2-(3-Ethoxy-4-methoxyphenyl)cyclohexyl]-4-p-tolylsulfamoylbenzamide Solidifying Oil A4. (−)-cis-N-[2-(3,4-Dimethoxyphenyl)cyclohexyl]-4-sulfamoylbenzamide Oil, specific rotation $[\alpha]_D^{20} = -118°$ (c=0.2; ethanol)

A5. (−)-cis-N-[2-(3,4-Dimethoxyphenyl)cyclohexyl]-4-p-tolylsulfamoylbenzamide

Solidifying Oil

Specific rotation $[\alpha]_D^{20} = -101°$ (c=0.2; ethanol)

A6. (+/−)-cis-N-[2-(3-Ethoxy-4-methoxyphenyl)cyclohexyl]-4-pyrid-3-ylamidobenzamide 3.0 g of (+/−)-cis-2-ethoxy-1-methoxy-4-(2-aminocyclohexyl)benzene (compound B1) are dissolved in 100 ml of methylene chloride and 20 ml of triethylamine. 3.76 g of 4-pyrid-3-ylamido benzoyl chloride are added in solid form at RT and the mixture is extracted after stirring overnight with 100 ml each of water, 2N hydrochloric acid, saturated sodium hydrogencarbonate solution and water again. The organic phase is dried using sodium sulfate and concentrated. The residue is extracted by stirring with ethyl acetate, filtered off with suction and dried. 1.6 g of the title compound of m.p. 167–174° C. are obtained.

Starting from the starting compounds described below, the following is obtained according to the procedure as in Example A6:

A7. (+/−)-cis-N-[2-(3-Ethoxy-4-methoxyphenyl)cyclohexyl]-4-cyanophenylamidobenzamide m.p.: 152–153° C.

B1. (+/−)-cis-2-Ethoxy-1-methoxy-4-(2-aminocyclo-hexyl)benzene 40.0 g of (+/−)-cis-2-ethoxy-1-methoxy-4-(2-nitrocyclohex-4-enyl)benzene (compound C1) are dissolved in 1000 ml of ethanol and 500 ml of tetrahydrofuran, treated with 10 g of Raney nickel and hydrogenated at a hydrogen pressure of 100 bar for 4 days in an autoclave. After filtration and removal of the solvent in vacuo, 35.9 g of the title compound are obtained as a solidifying oil.

B2. (+/−)-cis-1,2-Dimethoxy-4-(2-aminocyclohexyl)benzene 8.5 g of (+/−)-cis-1,2-dimethoxy-4-(2-nitrocyclohexyl)benzene are dissolved in 400 ml of methanol and treated with 7 ml of hydrazine hydrate and 2.5 g of Raney nickel in portions at RT in the course of 8 h. After stirring overnight at RT, the reaction mixture is filtered, the filtrate is concentrated and the residue is chromatographed on silica gel using a mixture of toluene/ethyl acetate/triethylamine=4/2/0.5. The title compound is obtained as an oil.

B3. (−)-cis-1,2-Dimethoxy-4-(2-aminocyclohexyl)benzene 12.0 g of (+/−)-cis-1,2-dimethoxy-4-(2-aminocyclohexyl)benzene and 6.2 g of (−)-mandelic acid are dissolved in 420 ml of dioxane and 60 ml of tetrahydrofuran and the solution is stirred at RT overnight. The solid is filtered off with suction, dried, treated with 100 ml of saturated sodium hydrogencarbonate solution and extracted with ethyl acetate. The organic phase is dried using sodium sulfate and concentrated under reduced pressure. 4.8 g of the title compound of m.p.: 80–81.5° C. are obtained.

Specific rotation: $[\alpha]_D^{20} = -58.5°$ (c=1, ethanol)

C1. (+/−)-cis-2-Ethoxy-1-methoxy-4-(2-nitrocyclohex-4-enyl)benzene 89.25 g of (+/−)-trans-2-ethoxy-1-methoxy-4-(2-nitrocyclohex-4-enyl)benzene (compound D1) and 37 g of potassium hydroxide are dissolved in 500 ml of absolute ethanol. A solution of 23.5 ml of conc. sulfuric acid in 120 ml of absolute ethanol is then added dropwise such that the internal temperature does not exceed −2° C. After stirring for 1 h, the mixture is added to 4 l of ice water, and the precipitate is filtered off with suction, washed with water and dried. M.p.: 66–67° C.

C2. (+/−)-cis-1,2-Dimethoxy-4-(2-nitrocyclohex-4-enyl) benzene 10.0 g of (+/−)-trans-1,2-dimethoxy-4-(2-nitrocyclohex-4-enyl)benzene and 20.0 g of potassium hydroxide are dissolved in 150 ml of ethanol and 35 ml of dimethyl formamide. A solution of 17.5 ml of conc. sulfuric acid in 60 ml of ethanol is then added dropwise such that the internal temperature does not exceed 4° C. After stirring for 1 h, the mixture is added to 1 l of ice water, the precipitate is filtered off with suction, washed with water and dried, and the crude product is recrystallized from ethanol. 8.6 g of the title compound of m.p. 82.5–84° C. are obtained.

C3. (+/−)-cis-1,2-Dimethoxy-4-(2-nitrocyclohexyl)benzene 8.4 g of (+/−)-cis-1,2-dimethoxy-4-(2-nitrocyclohex-4-enyl)benzene are dissolved in 450 ml of methanol, treated with 2 ml of conc. hydrochloric acid and hydrogenated after addition of 500 mg of 10% strength Pd/C. The reaction mixture is filtered and the filtrate is concentrated. M.p.: 84–86.5° C.

D1. (+/−)-trans-2-Ethoxy-1-methoxy-4-(2-nitrocyclohex-4-enyl)benzene 110 g of 3-ethoxy-2-methoxy-ω-nitrostyrene (compound E1) and 360 mg of hydroquinone are suspended in 360 ml of absolute toluene and treated at −70° C. with 180 ml of liquid 1,3-butadiene. The mixture is stirred at 160–180° C. for 6 days in an autoclave and then cooled. The product is extracted by stirring with ethanol, filtered off with suction and dried. M.p.: 130–131° C.

D2. (+/−)-trans-1,2-Dimethoxy-4-(2-nitrocyclohex-4-enyl) benzene 50.0 g of 3,4-dimethoxy-ω-nitrostyrene and 1.0 g (9.1 mmol) of hydroquinone are suspended in 200 ml of abs. toluene and treated at −70° C. with 55.0 g (1.02 mmol) of liquid 1,3-butadiene. The mixture is stirred at 160° C. for 6 days in an autoclave and then cooled. Some of the solvent is removed on a rotary evaporator, and the resulting precipitate is filtered off with suction and recrystallized in ethanol. M.p.: 113.5–115.5° C.

E1. 3-Ethoxy-2-methoxy)-ω-nitrostyrene 236 g of 3-ethoxy-2-methoxybenzaldehyde, 101 g of ammonium acetate and 320 ml of nitromethane are heated to 100° C. for 4 h in 655 ml of glacial acetic acid. The solution is added to 5 l of ice water, and the precipitate is filtered off with suction, washed with water and dried. M.p.: 132–133° C.

E2. 3,4-Dimethoxy-ω-nitrostyrene 207.0 g of 3,4-dimethoxybenzaldehyde, 100.0 g of ammonium acetate and 125 ml of nitromethane are heated to boiling for 3–4 h in 1.0 l of glacial acetic acid. After cooling in an ice bath, the precipitate is filtered off with suction, rinsed with glacial acetic acid and petroleum ether and dried. M.p.: 140–141° C. Yield: 179.0 g.

Commercial Utility

The compounds according to the invention have valuable pharmacological properties which make them commercially utilizable. As selective cyclic nucleotide phosphodiesterase (PDE) inhibitors (namely of type 4), they are suitable on the one hand as bronchial therapeutics (for the treatment of airway obstructions on account of their dilating but also on account of their respiratory rate- or respiratory drive-increasing action) and for the elimination of erectile dysfunction on account of the vasodilating action, but on the other hand especially for the treatment of disorders, in particular of inflammatory nature, e.g. of the airways (asthma prophylaxis), of the skin, of the central nervous system, of the intestine, of the eyes and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by low toxicity, good enteral absorption (high bioavailability), a large therapeutic breadth and the absence of significant side effects.

On account of their PDE-inhibiting properties, the compounds according to the invention can be employed as therapeutics in human and veterinary medicine, where they can be used, for example, for the treatment and prophylaxis of the following diseases: acute and chronic (in particular inflammatory and allergen-induced) airway disorders of various origins (bronchitis, allergic bronchitis, bronchial asthma); dermatoses (especially of proliferative, inflammatory and allergic nature) such as, for example, psoriasis (vulgaris), toxic and allergic contact eczema, atopic eczema, seborrheic eczema, lichen simplex, sunburn, pruritis in the anogenital area, alopecia areata, hypertrophic scars, discoid lupus erythematosus, follicular and wide-area pyodermias, endogenous and exogenous acne, acne rosacea and other proliferative, inflammatory and allergic skin disorders; disorders which are based on an excessively high release of TNF and leukotrienes, thus, for example, disorders of the arthritis type (rheumatoid arthritis, rheumatoid spondylitis, osteoarthritis and other arthritic conditions), disorders of the immune system (AIDS, multiple sclerosis), types of shock [septic shock, endotoxin shock, gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the area of the upper airways (nasopharynx, nose) and the adjacent regions (paranasal sinuses, eyes) such as, for example, allergic rhinitis/sinusitis, chronic rhinitis/sinusitis, allergic conjunctivitis and nasal polyps; but also disorders of the heart which can be treated by PDE inhibitors, such as, for example, cardiac insufficiency, or disorders which can be treated on account of the tissue-relaxant action of the PDE inhibitors, such as, for example, erectile dysfunction, colics of the kidneys and of the urinary tract in connection with kidney stones or alternatively disorders of the CNS, such as, for example, depression or arteriosclerotic dementia.

A further subject of the invention is a procedure for the treatment of mammals, including humans, who are suffering from one of the abovementioned diseases. The procedure comprises administering a therapeutically efficacious and pharmacologically tolerable amount of one or more of the compounds according to the invention to the sick mammal.

A further subject of the invention are the compounds according to the invention for use in the treatment and/or prophylaxis of diseases, in particular of the diseases mentioned.

The invention likewise relates to the use of the compounds according to the invention for the production of medicaments which are employed for the treatment and/or prophylaxis of the diseases mentioned.

Medicaments for the treatment and/or prophylaxis of the diseases mentioned, which contain one or more of the compounds according to the invention, are furthermore a subject of the invention.

The medicaments are prepared by methods known per se, which are familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on the basis of his expert knowledge with the auxiliaries which are suitable for the desired pharmaceutical formulations. In addition to solvents, gel-forming agents, ointment bases and other active compound excipients, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this purpose, these are either administered directly as a powder (preferably in micronized form) or by atomization of solutions or suspensions which contain them. With respect to the preparations and administration forms, reference is made, for example, to the details in European Patent 163 965.

For the treatment of dermatoses, the compounds according to the invention are used, in particular, in the form of those medicaments which are suitable for topical application. For the production of the medicaments, the compounds according to.the invention (=active compounds) are preferably mixed with suitable pharmaceutical auxiliaries and processed further to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by procedures known per se. The active compounds are administered in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.03 and 3 mg per kilogram per day.

Biological Investigations

In the investigation of PDE 4 inhibition on the cellular level, the activation of inflammatory cells is ascribed particular importance. An example which may be mentioned is the FMLP (N-formyl-methionylleucyl-phenylalanine)-induced superoxide production of neutrophilic granulocytes, which can be measured as luminol-potentiated chemoluminescence. [Mc Phail L C, Strum S L, Leone P A and Sozzani S, The neutrophil respiratory burst mechanism. In "Immunology Series" 1992, 57, 47–76; ed. Coffey R G (Marcel Decker, Inc., New York-Basel-Hong Kong)].

Substances which inhibit the chemoluminescence and the cytokine secretion and the secretion of proinflammatory mediators from inflammatory cells, in particular neutrophilic and eosinophilic granulocytes, T lymphocytes, monocytes and macrophages, are those which inhibit PDE 4. This isoenzyme of the phosphodiesterase families is particularly represented in granulocytes. Its inhibition leads to an increase in the intracellular cyclic AMP concentration and thus to the inhibition of cellular activation. PDE 4 inhibition by the substances according to the invention is thus a central indicator of the suppression of inflammatory processes. (Giembycz M A, Could isoenzyme-selective phosphodiesterase inhibitors render bronchodilatory therapy redundant in the treatment of bronchial asthma?. Biochem Pharmacol 1992, 43, 2041–2051; Torphy T J et al., Phosphodiesterase inhibitors: new opportunities for treatment of asthma. Thorax 1991, 46, 512–523; Schudt C et al., Zardaverine: a cyclic AMP PDE 3/4 inhibitor. In "New Drugs for Asthma Therapy", 379–402, Birkhäuser Verlag Basel 1991; Schudt C et al., Influence of selective phosphodiesterase inhibitors on human neutrophil functions and levels of cAMP and Ca; Naunyn-Schmiedebergs Arch Pharmacol 1991, 344, 682–690; Tenor H and Schudt C, Analysis of PDE isoenzyme profiles in cells and tissues by pharmacological methods. In "Phosphodiesterase Inhibitors", 21–40, "The Handbook of Immunopharmacology", Academic Press, 1996; Hatzelmann A et al., Enzymatic and functional aspects of dual-selective PDE3/4-inhibitors. In "Phosphodiesterase Inhibitors", 147–160, "The Handbook of Immunopharmacology", Academic Press, 1996.

Inhibition of PDE 4 Activity

Methodology

The activity test was carried out by the method of Bauer and Schwabe, which was adapted to microtiter plates (Naunyn-Schmiedeberg's Arch. Pharmacol. 1980, 311, 193–198). In this connection, the PDE reaction is carried out in the first step. In a second step, the resultant 5'-nucleotide is cleaved to give the uncharged nucleoside by a 5'-nucleotidase of the snake venom from *Crotalus atrox*. In the third step, the nucleoside is separated from the remaining charged substrate on ion exchange columns. The columns are eluted with 2 ml of 30 mM ammonium formate (pH 6.0) directly into minivials to which 2 ml of scintillation fluid is additionally added for counting.

The inhibitory values determined for the compounds according to the invention [inhibitory concentration as –log $IC_{50}$ (mol/l)] follow from Table A below, in which the numbers of the compounds correspond to the numbers of the examples.

TABLE A

| Inhibition of PDE 4 activity | |
| --- | --- |
| Compound | -log IC$_{50}$ |
| 1 | 8.55 |
| 2 | 9.25 |
| 3 | 9.24 |
| 5 | 8.30 |
| 6 | 8.66 |

What is claimed is:

1. A compound of formula I

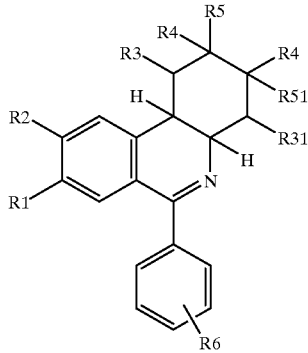

(I)

in which
R1 is hydroxyl, 1–4C-alkoxy, 3–7C-cycloalkoxy, 3–7C-cycloalkylmethoxy or completely or predominantly fluorine-substituted 1–4C-alkoxy,
R2 is hydroxyl, 1–4C-alkoxy, 3–7C-cycloalkoxy, 3–7C-cycloalkylmethoxy or completely or predominantly fluorine-substituted 1–4C-alkoxy,
or in which
R1 and R2 together are a 1–2C-alkylenedioxy group,
R3 is hydrogen or 1–4C-alkyl,
R31 is hydrogen or 1–4C-alkyl,
or in which
R3 and R31 together are a 1–4C-alkylene group,
R4 is hydrogen or 1–4C-alkyl,
R5 is hydrogen,
R51 is hydrogen,
or in which
R5 and R51 together are an additional bond,
R6 is SO$_2$—N(R7)R8 or CO—N(R9)R10, where
R7 and R8 independently of one another are hydrogen, 1–7C-alkyl, 3–7C-cycloalkyl, 3–7C-cycloalkylmethyl or an unsubstituted or R12- and/or R13-substituted phenyl radical, or where R7 and R8, together and including the nitrogen atom to which both are bonded, are a 1-pyrrolidinyl, 1-piperidyl, 1-hexahydroazepinyl or 4-morpholinyl radical,
R9 is hydrogen or 1–4C-alkyl,
R10 is an unsubstituted or R11-substituted pyridyl radical or an unsubstituted or R12- and/or R13- substituted phenyl radical, where
R11 is halogen, nitro, carboxyl, 1–4C-alkoxy, 1–4C-alkoxycarbonyl, 1–4C-alkyl, trifluoromethyl or completely or predominantly fluorine-substituted 1–4C-alkoxy,
R12 is hydroxyl, halogen, 1–4C-alkyl or 1–4C-alkoxy,
R13 is hydroxyl, halogen, nitro, cyano, carboxyl, 1–4C-alkyl, trifluoromethyl, 1–4C-alkoxy, 1–4C-alkoxycarbonyl, 1–4C-alkylcarbonyloxy, amino, mono- or di-1–4C-alkylamino, aminocarbonyl, mono- or di-1–4C-alkylaminocarbonyl or completely or predominantly fluorine-substituted 1–4C-alkoxy,
or salt thereof.

2. A compound of formula I as claimed in claim 1, in which
R1 is 1–4C-alkoxy, 3–7C-cycloalkoxy, 3–7C-cycloalkylmethoxy or completely or predominantly fluorine-substituted 1–2C-alkoxy,
R2 is 1–4C-alkoxy, 3–7C-cycloalkoxy, 3–7C-cycloalkylmethoxy or completely or predominantly fluorine-substituted 1–2C-alkoxy,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is SO$_2$—N(R7)R8, where
R7 and R8 independently of one another are hydrogen, 1–4C-alkyl, 3–7C-cycloalkyl, 3–7C-cycloalkylmethyl or an unsubstituted or R12- and/or R13-substituted phenyl radical, or where R7 and R8, together and including the nitrogen atom to which both are bonded, are a 1-piperidyl or 4-morpholinyl radical,
R12 is hydroxyl, halogen, 1–4C-alkyl or 1–4C-alkoxy,
R13 is hydroxyl, halogen, nitro, cyano, carboxyl, 1–4C-alkyl, trifluoromethyl, 1–4C-alkoxy, 1–4C-alkoxycarbonyl, 1–4C-alkylcarbonyloxy or completely or predominantly fluorine-substituted 1–4C-alkoxy,
or a salt thereof.

3. A compound of formula I as claimed in claim 1, in which
R1 is 1–4C-alkoxy, 3–7C-cycloalkoxy or completely or predominantly fluorine-substituted 1–2C-alkoxy,
R2 is 1–4C-alkoxy, 3–7C-cycloalkoxy or completely or predominantly fluorine-substituted 1–2C-alkoxy,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is SO$_2$—N(R7)R8, where
R7 and R8 independently of one another are hydrogen, 1–4C-alkyl, 3–7C-cycloalkyl or an unsubstituted or R13-substituted phenyl radical, where
R13 is halogen, nitro, cyano, 1–4C-alkyl, trifluoromethyl, 1–4C-alkoxy, 1–4C-alkoxycarbonyl, 1–4C-alkylcarbonyloxy or completely or predominantly fluorine-substituted 1–4C-alkoxy,
or a salt thereof.

4. A compound of formula I as claimed in claim 1, in which
R1 is 1–4C-alkoxy,
R2 is 1–4C-alkoxy,
R3, R31 and R4 are hydrogen,
R5 is hydrogen,
R51 is hydrogen,
or in which
R5 and R51 together are an additional bond,
R6 is SO$_2$—N(R7)R8, where
R7 and R8 independently of one another are hydrogen, 1–4C-alkyl or an unsubstituted or R13-substituted phenyl radical, where
R13 is halogen, cyano, 1–4C-alkyl or 1–4C-alkoxy,
or a salt thereof.

5. A compound of formula I as claimed in claim 1, in which
R1 is 1–4C-alkoxy, 3–7C-cycloalkoxy, 3–7C-cycloalkylmethoxy or completely or predominantly fluorine-substituted 1–2C-alkoxy,
R2 is 1–4C-alkoxy, 3–7C-cycloalkoxy, 3–7C-cycloalkylmethoxy or completely or predominantly fluorine-substituted 1–2C-alkoxy,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is CO—N(R9)R10, where
R9 is hydrogen,
R10 is an unsubstituted or R11-substituted pyridyl radical or an unsubstituted or R12- and/or R13-substituted phenyl radical, where
R11 is halogen, 1–4C-alkoxy, 1–4C-alkyl, trifluoromethyl or completely or predominantly fluorine-substituted 1–4C-alkoxy,
R12 is hydroxyl, halogen, 1–4C-alkyl or 1–4C-alkoxy,
R13 is hydroxyl, halogen, nitro, cyano, carboxyl, 1–4C-alkyl, trifluoromethyl, 1–4C-alkoxy, 1–4C-alkoxycarbonyl, 1–4C-alkylcarbonyloxy or completely or predominantly fluorine-substituted 1–4C-alkoxy,
or a salt thereof.

6. A compound of formula I as claimed in claim 1, in which
R1 is 1–4C-alkoxy, 3–7C-cycloalkoxy or completely or predominantly fluorine-substituted 1–2C-alkoxy,
R2 is 1–4C-alkoxy, 3–7C-cycloalkoxy or completely or predominantly fluorine-substituted 1–2C-alkoxy,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is CO—N(R9)R10, where
R9 is hydrogen,
R10 is an unsubstituted or R11-substituted pyridyl radical or an unsubstituted or R13-substituted phenyl radical, where
R11 is halogen, 1–4C-alkoxy, 1–4C-alkyl or trifluoromethyl,
R13 is halogen, nitro, cyano, 1–4C-alkyl, trifluoromethyl, 1–4C-alkoxy, 1–4C-alkoxycarbonyl, 1–4C-alkylcarbonyloxy or completely or predominantly fluorine-substituted 1–4C-alkoxy,
a salt thereof.

7. A compound of formula I as claimed in claim 1, in which
R1 is 1–4C-alkoxy,
R2 is 1–4C-alkoxy,
R3, R31 and R4 are hydrogen,
R5 is hydrogen,
R51 is hydrogen,
or in which
R5 and R51 together are an additional bond,
R6 is CO—N(R9)R10, where
R9 is hydrogen,
R10 is an unsubstituted pyridyl radical or an unsubstituted or R13-substituted phenyl radical, where
R13 is halogen, cyano, 1–4C-alkyl or 1–4C-alkoxy,
or a salt thereof.

8. A compound of formula I as claimed in claim 1, in which
R1 is 1–2C-alkoxy,
R2 is 1–2C-alkoxy,
R3, R31, R4, R5 and R51 are hydrogen,
R6 is SO$_2$—N(R7)R8 or CO—N(R9)R10, where
R7 is hydrogen or n-propyl,
R8 is hydrogen, n-propyl or p-toluyl,
R9 is hydrogen,
R10 is pyrid-3-yl or 4-cyanophenyl,
or a salt thereof.

9. In a method for treating a subject afflicted with a condition amenable to treatment with an active ingredient which is a phosphodiesterase inhibitor and which comprises administering to the subject an effective amount of the active ingredient, the improvement wherein said active ingredient is a compound of formula I, as claimed in claim 1, or a pharmaceutically-acceptable salt thereof.

10. A medicament composition comprising a compound of formula I as claimed in claim 1, or a pharmaceutically-acceptable salt thereof, together with a pharmaceutical auxiliary and/or excipient.

11. A method for producing a medicament composition by combining an active ingredient for treating an airway disorder with a suitable pharmaceutical auxiliary and/or excipient, wherein the active ingredient is a compound of formula I as claimed in claim 1 or a pharmaceutically-acceptable salt thereof.

* * * * *